US006299881B1

(12) United States Patent
Lees et al.

(10) Patent No.: US 6,299,881 B1
(45) Date of Patent: Oct. 9, 2001

(54) URONIUM SALTS FOR ACTIVATING HYDROXYLS, CARBOXYLS, AND POLYSACCHARIDES, AND CONJUGATE VACCINES, IMMUNOGENS, AND OTHER USEFUL IMMUNOLOGICAL REAGENTS PRODUCED USING URONIUM SALTS

(75) Inventors: Andrew Lees, Silver Spring, MD (US); James J. Mond, Jerusalem (IL)

(73) Assignee: Henry M. Jackson Foundation for the Advancement of Military Medicine, Rockville, MD (US)

( * ) Notice: Subject to any disclaimer, the term of this patent is extended or adjusted under 35 U.S.C. 154(b) by 0 days.

(21) Appl. No.: 09/045,679

(22) Filed: Mar. 23, 1998

Related U.S. Application Data

(60) Provisional application No. 60/041,781, filed on Mar. 24, 1997.

(51) Int. Cl.[7] ..................... A61K 39/385; A61K 39/02; C07K 17/10; C07D 487/00

(52) U.S. Cl. ..................... 424/194.1; 424/178.1; 424/193.1; 424/197.11; 424/146.1; 424/196.11; 424/201.1; 424/202.1; 424/203.1; 424/280.1; 424/256.1; 424/244.1; 424/236.1; 424/240.1; 424/239.1; 424/88; 424/89; 424/92; 530/403; 530/806; 530/404; 530/405; 530/406; 530/409; 530/411; 530/391.1; 435/188; 435/961; 435/964; 436/543

(58) Field of Search ..................... 424/184.1, 185.1, 424/170.1, 256.1, 178.1, 202.1, 196.11, 194.1, 242.1, 203.1, 193.1, 197.11, 146.1, 280.1, 278.1, 250.1, 201.1, 88, 92, 240.1, 236.1, 89, 239.1; 435/851.4, 34, 69.3, 69.1, 964, 69.7, 7.1, 6, 810, 188, 961, 543; 530/326, 325, 345, 409, 324, 387.1, 806, 411, 328–331, 404, 391.1, 403, 395, 405, 350, 333, 406; 560/38–40; 514/18, 19, 258; 260/998.2; 436/501, 89, 86, 90, 161; 935/15; 544/262, 1, 106, 180, 238, 278, 280, 359

(56) References Cited

U.S. PATENT DOCUMENTS

| 4,057,685 | | 11/1977 | McIntire ............................. 536/18 |
|---|---|---|---|
| 4,122,094 | * | 10/1978 | Woziwodzki ..................... 260/345.6 |
| 5,153,312 | * | 10/1992 | Porro ................................. 530/405 |
| 5,166,394 | | 11/1992 | Breipohl et al. ..................... 558/301 |
| 5,304,497 | * | 4/1994 | Boyd et al. ........................... 436/89 |
| 5,514,543 | * | 5/1996 | Grossman et al. ..................... 435/6 |
| 5,580,981 | * | 12/1996 | Carpino ............................... 544/262 |
| 5,585,100 | * | 12/1996 | Mond et al. ....................... 424/193.1 |
| 5,651,971 | * | 7/1997 | Lees ................................. 424/194.1 |
| 5,679,352 | * | 10/1997 | Chong et al. ..................... 424/256.1 |
| 5,693,326 | * | 12/1997 | Lees ................................. 424/194.1 |
| 5,773,007 | * | 6/1998 | Penney et al. .................. 424/197.11 |
| 5,811,102 | * | 9/1998 | Jennings et al. ............... 424/197.11 |
| 5,843,463 | * | 12/1998 | Krivan et al. ..................... 424/256.1 |
| 5,864,010 | * | 1/1999 | Cooke et al. ....................... 530/300 |
| 5,879,895 | * | 3/1999 | Babiuk et al. ....................... 435/7.1 |
| 5,955,571 | * | 9/1999 | Schwemler et al. ................. 530/300 |

FOREIGN PATENT DOCUMENTS

| 460 446 B1 | | 4/1993 | (EP) . |
|---|---|---|---|
| 0 569 086 A2 | * | 11/1993 | (EP) ..................................... 33/547 |
| WO 95/08348 | | 3/1995 | (WO) . |
| WO 96/29094 | | 9/1996 | (WO) . |

OTHER PUBLICATIONS

Griel et al., Carboxyactivation of peptide fragments with new coupling reagents., Pept. 1996, Proc. Eur. Pept. Symp., 24th (1998), Meeting Date 1996, 437–438.,Abstract Only.*

Zimmer et al., Synthesis and backbone cyclization studies of hexapeptides using the reagents TBTU, HBTU, DPPA, and PPA., Pept. 1992, Proc. Eur. Pept. Symp. 22nd (19930, Meeting Date 1992, 393–4., Abstract Only.*

Pettersson et al., "Molecular characterization of the 98–kilodalton iron regulated outer membrane protein of *Neisseria meningitidis*"., Infection and Immunity, Nov. 1993, pp. 4724–4733, vol. 61, No. 11.*

Boslego et al., "Gonorrhea vaccines"., Chapter 17, Vaccines and Immunotherapy, 1993, pergamon press, 1991.*

Peeters, et al., Pneumococcal Conjugate Vaccines, *Immunology Letters*, vol. 30, pp. 267–274, 1991.

PCT International Search Report, PCT/US98/05622, Mar. 24, 1998.

Andersson et al., "Synthesis of Oligosaccharides with Oligoethylene Glycol Spacers and Their Conversion into Glycoconjugates Using N, N, N', N'–tetramethyl(succinimido)uronium tetrafluoroborate as a Coupling Reagent," Glycoconjugate Journal, vol. 10 (1993), 461–465.

Bannwarth et al., "Bathophenanthroline–ruthenium (II) Complexes as Non–Radioactive Labels for Oligonucleotides which can be Measured by Time–Resolved Fluorescence Techniques," Helvetica Chimica Acta, vol. 71 (1988), 2085–2099.

Bannwarth & Knorr, "Formation of Carboxamides with N, N, N', N'–Tetramethyl (Succinimido) Uronium Tetrafluoroborate in Aqueous/Organic Solvent–Systems," Tetrahedron Letters, vol. 32, No. 9 (1991), 1157–1160.

Bayer & Wilchek, "Biotin–Binding Proteins: Overview and Prospects," Methods of Enzymology, vol. 184 (1990), 49–51.

Cassels et al., "Linear Epitopes of Colonization Factor Antigen I and Peptide Vaccine Approach to Enterotoxigenic *Escherichia coli*," Journal of Industrial Microbiology and Biotechnology, vol. 19 (1997), 66–70.

Chu et al., "Further Studies on the Immunogenicity of *Haemophilus influenzae* Type b and Pneumococcal Type 6A Polysaccharide–Protein Conjugates," Infection and Immunity, vol. 40 (1983), 245–56.

Dick et al., "Glycoconjugates of Bacterial Carbohydrate Antigens: A Survey and Consideration of Design and Preparation Factors," Conjugate Vaccines (Eds. Cruse, et al.), Karger, Basel (1989), 48–114.

Ellis et al. (Editors), Development and Clinical Uses of Haemophilus B. Conjugate Vaccines, Marcel Dekker, New York (1994), 1–498.

Grabarek & Gergely, "Zero–Length Crosslinking Procedure with the Use of Active Esters," Analytical Biochemistry, vol. 185 (1990), 131–35.

Hermanson, "Homobifunctional Cross–linkers," Bioconjugate Techniques, Academic Press, San Diego (1996), vii–xx, 187–227.

Inman, "Thymus–Independent Antigens: The Preparation of Covalent, Hapten–Ficoll Conjugates," Journal of Immunology, vol. 114 (1975), 704–709.

Knorr et al., "New Coupling Reagents in Peptide Chemistry," Tetrahedron Letters, vol. 30, No. 15 (1989), 1927–1930.

Lees et al., "Activation of Soluble Polysaccharides with 1–cyano–4–dimethylamino pyridinium tetrafluoroborate For Use in Protein–Polysaccharide Conjugate Vaccines and Immunological Reagents," Vaccine, vol. 14, No. 3 (1996), 190–198.

Lees et al., "Enhanced Immunogenicity of Protein–Dextran Conjugates: I. Rapid Stimulation of Enhanced Antibody Responses to Poorly Immunogenic Molecules," Vaccine, vol. 12, No. 13 (1994), 1160–1166.

Lefevre et al., "Texas Red–X and Rhodamine Red–X, New Derivatives of Sulforhodamine 101 and Lissamine Rhodamine B with Improved Labeling and Fluorescence Properties," Bioconjugate Chemistry, vol. 7 (1996), 482–489.

Martin, Remington's Pharmaceutical Sciences, 18th Edition (1994), 1435–1711, 1389–1404.

Moller et al., "Versatile Procedure of Multiple Introduction of 8–Aminomethylene Blue into Oligonucleotides," Bioconjugate Chemistry, vol. 6 (1995), 174–178.

Monsigny et al., "Colorimetric Determination of Neutral Sugars by a Resorcinol Sulfuric Acid Micromethod," Anal. Biochemistry, vol. 175 (1988), 525–530.

Qi et al., "Spectrophotometric Determination of Hydrazine, Hydrazides, and Their Mixtures with Trinitrobenzenesulfonic Acid," Anal. Biochemistry, vol. 175 (1988), 139–144.

Szu et al., "Vi Capsular Polysaccharide–Protein Conjugates for Prevention of Typhoid Fever," Journal of Experimental Medicine, vol. 166 (1987), 1510–1524.

Vidal & Franci, Letter to the Editors, J. Immunol. Meth., vol. 86 (1986), 155–156.

Wilchek & Miron, "Limitations of N–Hydroxysuccinimide Esters in Affinity Chromatography and Protein Immobilization," Biochemistry, vol. 26 (1987), 2155–2161.

Wilchek et al., "Improved Method for Preparing N–Hydroxysuccinimide Ester–Containing Polymers for Affinity Chromatography," Bioconjugate Chemistry, vol. 5 (1994), 491–92.

Wong et al., "Standardization and Control of Meningococcal Vaccines, Group A and Group C Polysaccharides," Journal of Biological Standardization, vol. 5 (1977), 197–215.

* cited by examiner

*Primary Examiner*—Long V. Le
*Assistant Examiner*—Lisa J. Cook
(74) *Attorney, Agent, or Firm*—Finnegan, Henderson, Farabow, Garrett & Dunner, L.L.P.

(57) ABSTRACT

A method for producing a conjugate vaccine includes mixing a uronium salt reagent with a first moiety (e.g., a polysaccharide). According to the invention, the uronium salt reagent has a chemical structure corresponding to formula I:

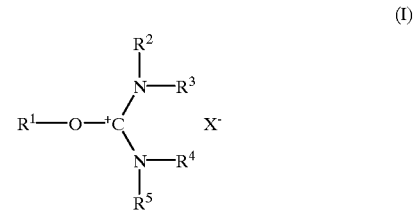

wherein $R^1$ is defined as

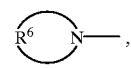

wherein $R^6$ represents the carbon, hydrogen, and optionally one or more heteroatoms which, together with the nitrogen atom to which they are attached, constitute a 5 to 10 membered heterocyclic ring, which may be substituted or unsubstituted. $R^2$, $R^3$, $R^4$, and $R^5$, each independently represents a hydrogen atom, a substituted or unsubstituted alkyl having 1 to 6 carbon atoms, a substituted or unsubstituted alkenyl having 2 to 6 carbon atoms, or an alkynyl having 2 to 6 carbon atoms. Alternatively, $R^2$ and $R^3$, when taken together, can represent the carbon, hydrogen, sulfur, nitrogen, or oxygen atoms necessary to complete a 5 to 7 membered heterocyclic ring with the nitrogen atom to which they are attached. Likewise, $R^4$ and $R^5$, when taken together, can represent a similar heterocyclic ring. $X^-$ represents an acid anion (e.g., $Cl^-$, $Br^-$, $F^-$, $I^-$, $PF_6^-$, and $BF_4^-$). Also in this method, a second moiety (e.g., a protein, a peptide, or a lipoprotein) is mixed with the first moiety. The first moiety and the second moiety react together to form a conjugate.

20 Claims, 1 Drawing Sheet

URONIUM SALTS FOR ACTIVATING HYDROXYLS, CARBOXYLS, AND POLYSACCHARIDES, AND CONJUGATE VACCINES, IMMUNOGENS, AND OTHER USEFUL IMMUNOLOGICAL REAGENTS PRODUCED USING URONIUM SALTS

RELATED APPLICATION DATA

This application claims priority benefits under 35 U.S.C. §119 based on U.S. Provisional Patent Application Ser. No. 60/041,781, filed Mar. 24, 1997, which application is entirely incorporated herein by reference.

BACKGROUND OF THE INVENTION

Vaccines have been very effective in protecting people from a wide variety of diseases, whether caused by viruses, bacteria, or fungi. The ability of vaccines to induce specific protection against such a wide range of pathogenic organisms results from their ability to stimulate specific humoral antibody responses, as well as cell-mediated responses. This invention relates to a process for preparing such vaccines, and particularly to a process for making conjugates that are used in preparing vaccines. Additionally, the process of the invention can be used to produce immunogens and other valuable immunological, therapeutic, or diagnostic reagents. The invention further relates to the vaccines, immunogens, and reagents produced from the conjugates made according to the invention, as well as to the use of these products.

It is often very desirable to induce immune responses against polysaccharides. For example, antibodies against a bacterial capsular polysaccharide can provide protection against that bacterium. Many polysaccharides, however, are poorly immunogenic, particularly in infants and young children. Furthermore, in both children and adults, there is usually no booster effect with repeated polysaccharide immunizations, and the principal antibody class is IgM. These features are all characteristic of so called "T cell independent" ("TI") antigens.

In many cases, the immunogenicity of polysaccharides can be enhanced by covalently linking proteins or T cell epitope-containing peptides to the polysaccharide. Certain other components, such as lipids, fatty acids, lipopolysaccharides, and lipoproteins, also are known to enhance the immunogenicity of the polysaccharide. As described in the "dual conjugate" patent application of Mond and Lees, conjugation of a protein to a polysaccharide can enhance the immune response to the protein as well as to the polysaccharide. See U.S. Pat. No. 5,585,100; U.S. patent application Ser. No. 08/444,727 (filed May 19, 1995); and U.S. patent application Ser. No. 08/468,060 (filed Jun. 6, 1995). These patent applications each are entirely incorporated herein by reference. This effect also is described in A. Lees, et al., "Enhanced Immunogenicity of Protein-Dextran Conjugates: I. Rapid Stimulation of Enhanced Antibody Responses to Poorly Immunogenic Molecules," Vaccine, Vol. 12, No. 13, (1994), pp. 1160–1166. This article is entirely incorporated herein by reference. In view of this potential for improving the immune response against polysaccharides, there is a need in the art for methods to covalently link proteins or other moieties to polysaccharides.

Ideally, the process of covalently linking moieties to a polysaccharide must be done in a way to maintain antigenicity of both the polysaccharide and protein components and to minimize damage to necessary epitopes of each component. Furthermore, the linkage should be stable.

Therefore, there is a need for a mild and gentle means for coupling proteins, peptides, haptens, organic molecules, or other moieties to polysaccharides.

Vaccines are not the only products that can benefit from an improved procedure for coupling molecules together. For example, certain diagnostic or therapeutic reagents are produced by coupling polysaccharides, high molecular weight carbohydrates, and low molecular weight carbohydrates to solid phase materials (e.g., solid particles or surfaces). Thus, there is a need in the art for improved means for coupling polysaccharides, high molecular weight carbohydrates, and low molecular weight carbohydrates to solid phase materials.

Two main methods for coupling molecules together are used. In the first method, the means for coupling entails the crosslinking of a protein (or peptide or other moiety) directly to a polysaccharide (or some other moiety). Sometimes, however, a spacer molecule is needed between the coupled moieties, either to facilitate the chemical process and/or to enhance the immune response to the protein and/or the polysaccharide. In either method, it is usually necessary to activate or functionalize the polysaccharide before crosslinking occurs. Some methods of activating or functionalizing polysaccharides are described in W. E. Dick, et al., "Glycoconjugates of Bacterial Carbohydrate Antigens: A Survey and Consideration of Design and Preparation Factors," Conjugate Vaccines (Eds. Cruse, et al.), Karger, Basel, 1989, Vol. 10, pp. 48–114. This excerpt is entirely incorporated herein by reference. Additional activation methods are described in R. W. Ellis, et al. (Editors), Development and Clinical Uses of Haemophilus B Conjugate Vaccines, Marcel Dekker, New York (1994), which book is entirely incorporated herein by reference.

One preferred method for activating polysaccharides is described in the CDAP patent applications of Lees, U.S. patent application Ser. No. 08/124,491 (filed Sep. 22, 1993, now abandoned); U.S. Pat. Nos. 5,651,971; 5,693,326; and U.S. patent application Ser. No. 08/482,666 (filed Jun. 7, 1995). These U.S. patents and patent applications each are entirely incorporated herein by reference. The use of CDAP also is described in Lees, et al., "Activation of Soluble Polysaccharides with 1-Cyano-4-Dimethylamino Pyridinium Tetrafluoroborate for Use in Protein-Polysaccharide Conjugate Vaccines and Immunological Reagents," Vaccine, Vol. 14, No. 3 (1996), pp. 190–198. This article also is entirely incorporated herein by reference.

One specific method of preparing conjugates is through the condensation of amines (or hydrazides) and carboxyls to amides using carbodiimides. The carboxyl nucleophile reacts with the carbodiimide to form a highly reactive but unstable intermediate that can then either hydrolyze or react with an amine to form a stable amide bond. 1-(3-dimethylaminopropyl)-3-ethylcarbodiimide ("EDC") is a water soluble example of this class of carbodiimide reagent.

As one example of this reaction, Robbins describes functionalizing Haemophilus influenza ("PRP") polysaccharide with hydrazides and condensing this functionalized material with carboxyls on tetanus toxoid. See C. Chu, et al., Infection and Immunity, Vol. 40, 1983, beginning at pg. 245. Additionally, the coupling of a carboxylated polysaccharide to diptheria toxoid by this general process also is described by Robbins. See S. C. Szu, et al., Journal of Experimental Medicine, Vol. 166, 1987, beginning at page 1510. These articles each are entirely incorporated herein by reference.

In general, however, there are a myriad of problems when one attempts to use carbodiimide for coupling multivalent ligands (e.g., proteins and polysaccharides) that contain both activatable groups and nucleophiles. The reaction is difficult to control, and it frequently leads to extensive homopolymerization, interchain crosslinking, and reduced antigenicity. A further problem is that the carboxyl-carbodiimide intermediate can undergo an O to N acyl shift, resulting in a stable, unreactive addition product that adds new epitopes to the protein (see G. T. Hermanson, *Bioconjugate Techniques,* Academic Press, San Diego, Calif., (1996), which document is entirely incorporated herein by reference).

Another method of forming conjugates is through the use of active ester intermediates. Reagents that form active ester intermediates include norborane, p-nitrobenzoic acid, NHS (N-hydroxysuccinimide), and S-NHS (sulfo-N-hydroxysuccinimide). NHS esters (or other suitable reagents) can react with nucleophiles like amines, hydrazides, and thiols. The reaction products of NHS esters with amines and hydrazides are particularly stable, forming an amide bond. NHS ester intermediates can be formed in a one step process using carbodiimide (to activate the carboxyls) and NHS (or S-NHS). In this process, NHS (or S-NHS), the carboxyl-containing component, and the amine-containing component are combined, and the carbodiimide is added thereto. Although coupling efficiency often is higher in this reaction than is the case when NHS is not present, problems, such as homopolymerization, interchain crosslinking, and over-crosslinking, can occur in this process. Additionally, other undesirable side reactions can occur and cause problems, as will be described in more detail below.

Alternatively, a two step activation process can be used. In this procedure, one attempts to remove or destroy the remaining carbodiimide before adding the component to be crosslinked. In one protocol using EDC and NHS, before adding the protein, the remaining carbodiimide is deactivated with a thiol (e.g., mercaptoethanol). See Grabarek and Gergely, *Analytical Biochemistry,* Vol. 185 (1990), beginning at pg. 131, which article is entirely incorporated herein by reference. By this method, the amount of carbodiimide present during protein addition is minimized. The addition of the thiol, however, also can hydrolyze the desired NHS ester intermediate. In this two step process, it would be preferable to isolate the NHS ester intermediate. It can be difficult, however, to isolate this intermediate because it is only moderately stable in aqueous media.

An additional problem with carbodiimide/NHS procedures is the possible formation of a β-alanine derivative resulting from the reaction of carbodiimide with two moles of NHS in a Lossen rearrangement (see Wilchek and Miron, *Biochemistry,* Vol. 26, beginning at pg. 2155, 1987, which article is entirely incorporated herein by reference). This derivative can react with amines to form an unstable crosslink.

Carbodiimide and NHS also have been used to activate oligosaccharides. In such procedures, the reducing ends of oligosaccharides are functionalized with carboxyl groups and then converted to active esters using carbodiimide and NHS in organic solvents. These functionalized oligosaccharides are then coupled to proteins. See Porro, U.S. Pat. No. 5,153,312 (Oct. 6, 1992) for the use of this procedure with an oligosaccharide from *Neisseria meningiditis* polysaccharide type C. This patent is entirely incorporated herein by reference. The reported overall coupling efficiency, however, is low, and low molecular weight oligosaccharides are used. One reason for the low coupling efficiency is that the oligosaccharides have only one NHS per molecule. It either hydrolyzes or couples.

A variety of other reagents are known for introducing NHS esters; however, most of these require dry organic solvents and are unsuitable for use in aqueous media. One exception includes certain uronium salts, such as the reagent O-(N-succinimidyl) N,N,N',N'-tetramethyluronium tetrafluoroborate (TSTU), which are somewhat stable in water, although more so in mixed organic/aqueous media. TSTU has been used to form NHS esters of low molecular weight molecules in organic solvents (see Moller et al., "Versatile Procedure of Multiple Introduction of 8-Aminomethylene Blue into Oligonucleotides," *Bioconjugate Chemistry,* Vol. 6 (1995), pp. 174–178; Lefevre et al., "Texas Red-X and Rhodarnine Red-X, New Derivatives of Sulforhodamine 101 and Lissamine Rhodamine B with Improved Labeling and Fluorescence Properties," *Bioconjugate Chemistry,* Vol. 7 (1996), pp. 482–489; and Bannwarth et al., "219, Bathophenanthroline-ruthenium (II) Complexes as Non-Radioactive Labels for Oligonucleotides which can be Measured by Time-Resolved Fluorescence Techniques," *Helvetica Chimica Acta,* Vol. 71 (1988), beginning at pg. 2085, which articles each are entirely incorporated herein by reference.) Additionally, TSTU and other uronium salts have been used to form NHS esters of low molecular weight molecules in mixed organic/aqueous media (see Knorr et al.,"New Coupling Reagents in Peptide Chemistry," *Tetrahedron Letters,* Vol. 30, No. 15 (1989), pp. 1927–1930; and Bannwarth and Knorr, "Formation of Carboxamides with N,N,N',N'-Tetramethyl (Succinimido) Uroniumn Tetrafluoroborate in Aqueous/Organic Solvent-Systems," *Tetrahedron Letters,* Vol. 32, No. 9 (1991), pp. 1157–1160, which articles also are entirely incorporated herein by reference).

TSTU also has been used to prepare active esters of solid phase carboxylated beads in organic solvents (see Wilchek et al., "Improved Method for Preparing N-Hydroxysuccinimide Ester-Containing Polymers for Affinity Chromatography," *Bioconjugate Chemistry,* Vol. 5 (1994), pp. 491–492, which article is entirely incorporated herein by reference). Reagents like TSTU are advantageous over the carbodiimide/NHS method because there is a reduced likelihood of various side reactions, such as an O to N shift reaction or a Lossen rearrangement.

M. A. Andersson, et al., "Synthesis of oligosaccharides with oligoethylene glycol spacers and their conversion into glycoconjugates using N,N,N',N'-tetramethyl(succinimido) uronium tetrafluoroborate as a coupling reagent," *Glycoconjugate Journal,* Vol. 10 (1993), pp. 461–465, which article is entirely incorporated herein by reference, describes the use of TSTU to activate a carboxylated saccharide in a mixed aqueous/organic solvent and the subsequent coupling of this activated material to a protein. Andersson does not describe the use of this method for producing vaccines.

European Patent Application No. 0,569,086 A2 (S. J. Danielson et al.) describes the use of TSTU and similar reagents for preparing active esters of insoluble carboxylated substrates and particles. These activated solids are subsequently coupled to biologically relevant molecules to prepare diagnostic reagents. This document is entirely incorporated herein by reference.

Despite the various coupling and activation methods described in the various documents mentioned above, there is an on-going need in the art for improved methods for coupling biologically relevant molecules to one another to produce vaccines. Additionally, there is a need in the art for an improved procedure for coupling biologically relevant molecules to non-carboxylated surfaces and particles to produce various reagents. This invention seeks to provide an improved coupling method for producing conjugates for vaccines and immunogens. In addition, these methods will be useful for producing immunological reagents, diagnostic reagents, and therapeutic reagents.

SUMMARY OF THE INVENTION

This invention relates to a method for producing a conjugate, and advantageously, conjugate vaccines. In this method, a first moiety (e.g., a polysaccharide, a high or low molecular weight carbohydrate, a hydroxylated compound (such as polyvinyl alcohol), etc.) is activated with a uronium salt reagent. The uronium salt reagent is believed to activate carboxyl groups or hydroxyl groups present on the first moiety, although Applicants do not wish to be bound by any specific chemical mechanisms or theories of operation. The first moiety can be present in an aqueous media, in a mixture of an aqueous/organic media, or in an organic media. According to the process of the invention, the uronium salt reagent has a chemical structure corresponding to formula I:

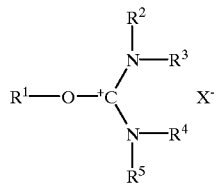

(I)

wherein:
R$^1$ is defined as

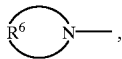

wherein R$^6$ represents the carbon atoms, hydrogen atoms, and optionally one or more heteroatoms, which, together with the nitrogen atom to which they are attached, constitute a 5 to 10 membered heterocyclic ring, which may be substituted or unsubstituted.

R$^2$ and R$^3$ are defined as follows:

R$^2$ represents a hydrogen atom, a substituted or unsubstituted alkyl having 1 to 6 carbon atoms, a substituted or unsubstituted alkenyl having 2 to 6 carbon atoms, or an alkynyl having 2 to 6 carbon atoms;

R$^3$ represents a hydrogen atom, a substituted or unsubstituted alkyl having 1 to 6 carbon atoms, a substituted or unsubstituted alkenyl having 2 to 6 carbon atoms, or an alkynyl having 2 to 6 carbon atoms; or R$^2$ and R$^3$, when taken together, represent the carbon, hydrogen, sulfur, nitrogen, and/or oxygen atoms necessary to complete a 5 to 7 membered heterocyclic ring with the nitrogen atom to which they are attached, wherein the heterocyclic ring can be substituted or unsubstituted.

R$^4$ and R$^5$ are defined as follows:

R$^4$ represents a hydrogen atom, a substituted or unsubstituted alkyl having 1 to 6 carbon atoms, a substituted or unsubstituted alkenyl having 2 to 6 carbon atoms, or an alkynyl having 2 to 6 carbon atoms;

R$^5$ represents a hydrogen atom, a substituted or unsubstituted alkyl having 1 to 6 carbon atoms, a substituted or unsubstituted alkenyl having 2 to 6 carbon atoms, or an alkynyl having 2 to 6 carbon atoms; or R$^4$ and R$^5$, when taken together, represent the carbon, hydrogen, sulfur, nitrogen, and/or oxygen atoms necessary to complete a 5 to 7 membered heterocyclic ring with the nitrogen atom to which they are attached, wherein the heterocyclic ring can be substituted or unsubstituted.

X$^-$ represents an acid anion (e.g., Cl$^-$, Br$^-$, F$^-$, I$^-$, PF$_6^-$, and BF$_4^-$). Other suitable acid anions for use in this invention are described in European Patent Appl. No. 0,569,086.

Also, in the method of the invention, a second moiety (e.g., a protein, a peptide, a hapten, a lipoprotein, a carbohydrate, an organic molecule, a spacer molecule, a solid phase material, a homobifunctional reagent, a heterobifunctional reagent, etc.) is mixed with the first moiety. The first moiety is activated and reacts with the second moiety to form a conjugate or a functionalized first moiety.

One preferred class of uronium salt reagents for use in the invention includes the salts of formula I wherein the

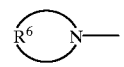

group is a member selected from the group of:

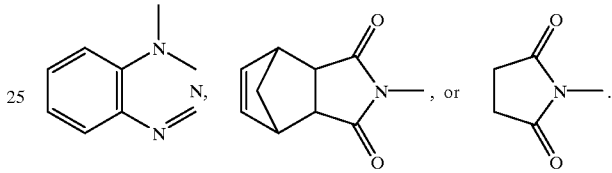

Specific reagents of this class include: 2-(1H-Benzotriazole-1-yl)-1,1,3,3-tetramethyluronium hexafluorophosphate ("HBTU"); 2-(1H-Benzotriazole-1-yl)- 1,1,3,3-tetramethyluronium tetrafluoroborate ("TBTU"); 2-(5-Norbornene-2,3-dicarboximido)-1,1,3,3-tetramethyluronium tetrafluoroborate ("TNTU"); and O-(N-Succinimidyl)-1,1,3,3-tetramethyluronium tetrafluoroborate ("TSTU"). Other suitable uronium salt activating reagents for use in this invention are described in European Patent Appl. No. 0,569,086.

In the method of the invention, the uronium salt reagent can be mixed with the first moiety before the second moiety is mixed with the first moiety. This initiates an activation reaction between the uronium salt reagent and the first moiety. In this first step, the first moiety is activated by the uronium salt reagent, and thereafter, the second moiety is mixed with the activated first moiety. Optionally, the activated first moiety can be isolated from the reaction mixture before the second moiety is mixed in, and then the second moiety can be mixed with the isolated product that includes the uronium salt activated first moiety.

As another alternative procedure, the second moiety can be mixed with the first moiety before the uronium salt reagent is mixed with the first moiety. In this manner, when the uronium salt is mixed with the mixture of the first and second moieties, the first moiety is activated by the uronium salt reagent, and the reaction between the activated first moiety and the second moiety proceeds in a single step. A single step reaction process also can occur when the uronium salt reagent and the second moiety are simultaneously mixed with the first moiety.

If desired, the first moiety can be functionalized with one or more chemical groups that are capable of being activated by the uronium salt. For example, a polysaccharide can be functionalized with carboxyls. This can be achieved, for example, by activating the first moiety (e.g., a polysaccharide or a high or low molecular weight carbohydrate) with a reagent selected from the group of CNBr, CDAP, and a vinylsulfone reagent, followed by reaction with 6-aminohexanoic acid.

The invention further relates to the reaction products produced by the process of the invention. These reaction products may include conjugates (including protein/polysaccharide conjugates) and conjugate vaccines (including protein/polysaccharide conjugate vaccines). The invention also can be used to produce immunogens, immunological reagents, therapeutic reagents, or diagnostic reagents. The invention also relates to methods for using these reaction products for their intended purpose. For example, the invention relates to methods of inducing an immune response in a subject by administering a conjugate vaccine to the subject. As such, the invention can be used to prevent, treat, diagnose, or ameliorate the symptoms of various diseases or ailments.

The process of producing a conjugate according to this invention has several advantages over the various methods and processes disclosed in the above-noted documents. None of the documents noted above describes the use of uronium salt reagents to form conjugate vaccines. The process of the invention, on the other hand, is a straightforward and easy method for producing conjugate vaccines. The process of the invention advantageously can be performed in the solution phase and can be used with both carboxylated and non-carboxylated polysaccharides. In addition, the reaction can proceed using small quantities of reagents, allowing one to quickly, efficiently, and inexpensively determine optimum reaction conditions. Unlike many known coupling methods, the process of the invention also allows for direct coupling of the first and second moieties (e.g., the protein and polysaccharide materials). This further simplifies the reaction procedure and reduces the costs.

Furthermore, the process of the invention is advantageous because it uses relatively safe reagents and mild reaction conditions (e.g., low pH, no hood or other special facilities). Many polysaccharides, such as PRP polysaccharide, are easily hydrolyzed at extreme pHs. The conditions used during uronium salt activation and coupling are relatively mild and gentle so that important epitopes are retained on the polysaccharide (i.e., minimal modifications of the protein and polysaccharide starting materials are induced). CNBr activation, on the other hand, requires the use of a high pH and a highly toxic reagent under a hood.

Another advantage of the invention relates to the one step procedure described above. Because the protein and polysaccharide components (or other moieties) can be mixed together before activation and coupling is initiated, the method of the invention allows one to continue adding fresh reagent and removing excess reagents until a sufficient and desired level of coupling is achieved. This is not readily possible with other activation methods, especially those methods that require activation of the polysaccharide followed by addition of the protein. The method of the invention also allows one to monitor the progress of the coupling during the conjugation procedure, thereby limiting waste or excessive use of the various reagents.

BRIEF DESCRIPTION OF THE DRAWING

The advantageous aspects of the invention will be more fully understood and appreciated when considered in conjunction with the following detailed description and the attached figure, wherein.

DETAILED DESCRIPTION OF THE INVENTION

Figure 1:
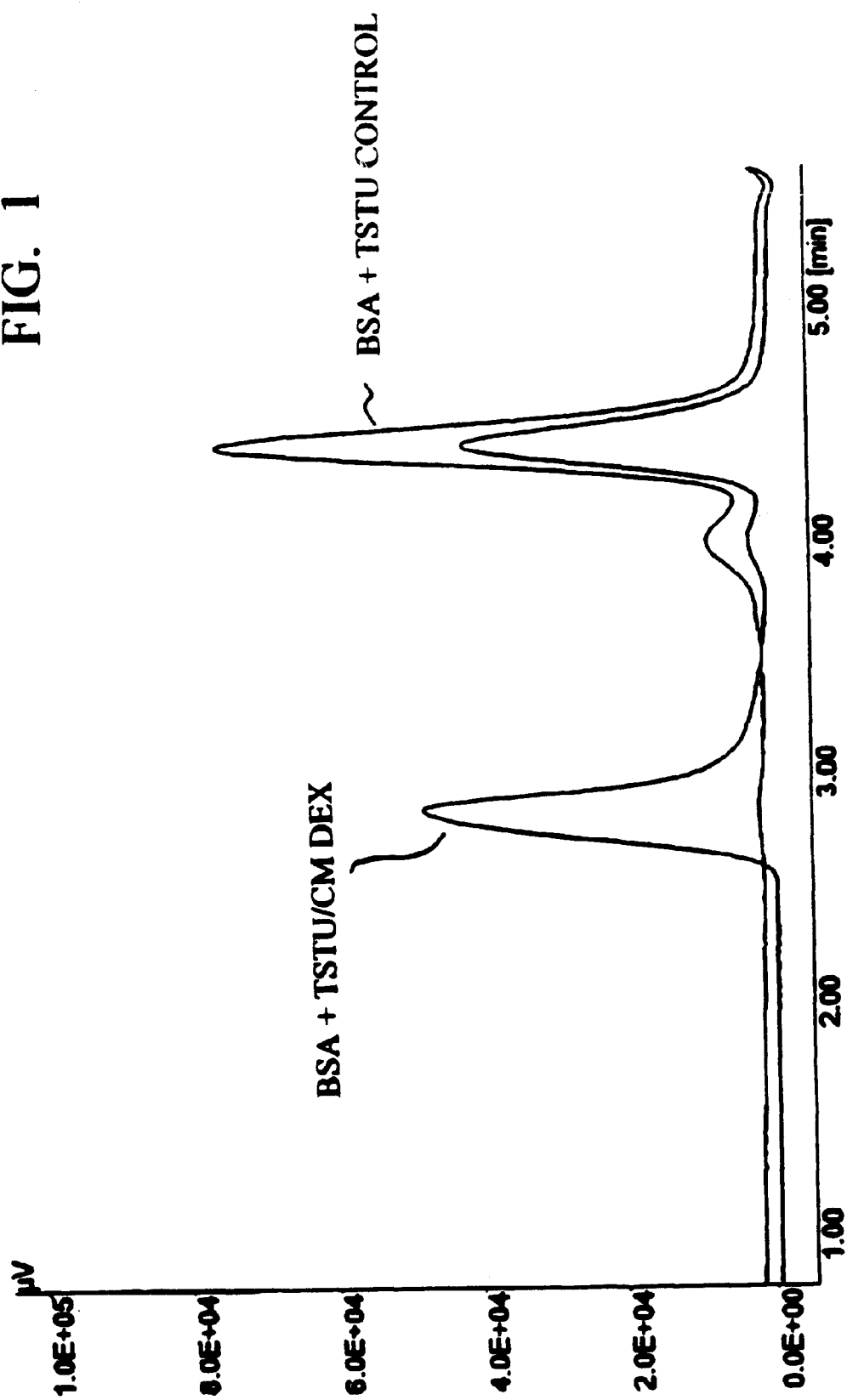
FIG. 1 illustrates HPLC runs for Samples 1A and 1C in Example 1 described below.

In accordance with the invention, polysaccharides, high or low molecular weight carbohydrates, or other moieties are activated with uronium salt reagents, such as TSTU, TNTU, HBTU, or TBTU, so they may be coupled to proteins, haptens, peptides, or other moieties. The invention further relates to the conjugates produced by the method of the invention, which conjugates can be used in preparing vaccines, immunological reagents, diagnostic reagents, therapeutic reagents, immunogens, and the like. The invention also relates to methods of using the conjugates of the invention as vaccines or reagents. The conjugate vaccines of the invention can be administered to a subject to induce an immune response.

The procedure of the invention is generally described as follows. A first moiety is reacted with a uronium salt reagent in a suitable environment to transfer an NHS-ester to the first moiety. For example, in accordance with the invention, a polysaccharide can be reacted with TSTU reagent in a base, such as dimethylaminopyridine ("DMAP") base. This reaction can take place in an aqueous media, in a mixed organic/aqueous media, or in an organic media. Various organic solvents can be used, including acetonitrile, dimethylformamide ("DMF"), and N-methylpyrrolidinone ("NMP"). A mildly basic pH generally is maintained during the reaction (e.g., 8 to 9.5), if necessary, by adding more base. The second moiety (e.g., a protein) is mixed with the first moiety at some time during this procedure.

The amount of uronium salt reagent can be adjusted and the activation time varied to optimize the activation and coupling efficiency. The addition of the uronium salt reagent can be staggered to minimize excess uronium salt reagent in the reaction at any given time. If desired, old or excess uronium salt reagent can be removed, e.g., by dialysis or ultrafiltration, before new reagent is mixed with the protein/polysaccharide mixture. In this manner, one can minimize the amount and percentage of organic solvent in the mixture and also maintain the protein and polysaccharide concentration at an optimum level to facilitate good coupling. This reagent removal step offers a level of control over the coupling because small amounts of activating reagent can be added, as necessary, and the progress of the conjugation reaction procedure can be monitored (e.g., by analyzing aliquots of the reaction mixture). This procedure also offers possibilities for scaling up the conjugation procedure. Those skilled in the art will be capable of determining optimum reaction conditions (such as pH and reaction time), reagent amounts, and reagent concentrations through routine experimentation.

Any conjugation procedure can be followed without departing from the invention. For example, in one procedure, a carboxylated polysaccharide is used as the starting material. This can be accomplished by starting with a polysaccharide that naturally contains carboxyl groups, such as *Neisseria meningiditis* polysaccharide type C ("Neisseria PsC"). Alternatively, carboxyl groups can be added to a polysaccharide. A variety of procedures are known to those skilled in the art for carboxylating polysaccharides. For example, polysaccharides can be activated with CNBr or CDAP and carboxylated with an appropriate reagent, such as 6-aminohexanoic acid. CNBr activation is described by W. E. Dick, supra., and CDAP activation is described in the patent applications and articles of Lees described above. Vinyl sulfone reagents also can be used to activate polysaccharides, as described in U.S. Provisional Patent Appln. No. 60/017,103 in the name of Andrew Lees, filed May 9, 1996, and U.S. patent application Ser. No. 08/852,733, filed May 7, 1997, which applications are entirely incorporated herein by reference.

In a one step protocol according to the invention, the first moiety and the second moiety are mixed first, and the uronium salt reagent then is mixed in. The uronium salt reagent can be added in small amounts at a plurality of different times. The first moiety is activated and reacts with the second moiety.

This one step protocol is described in more detail in the following general example. First, a first moiety (e.g., a polysaccharide) is mixed with a second moiety (e.g., a protein). Then, a uronium salt reagent (e.g., TNTU or TSTU) is mixed with this mixture, followed by the addition of a base material (e.g., triethylamine ("TEA")). Under this procedure, the operator can continue adding additional TNTU and/or TEA until a sufficient or desired level of coupling is observed. In fact, the reaction procedure and degree of coupling can be determined at various different times by analyzing aliquots of the reaction mixture as the reaction proceeds.

In a two step protocol according to the invention, the first moiety (e.g., a polysaccharide) is activated with a uronium salt reagent, and thereafter, the second moiety (e.g., a protein) is mixed with the activated first moiety. The buffer, reagent concentration, time, and temperature conditions, etc. can be selected such that at the time the second moiety (i.e., the component to be linked) is mixed in, the concentration of the activating reagent is too low to cause significant polymerization of that component. Due to the relative stability of the NHS-ester and their multiplicity on the first moiety, there can still be a sufficient number of activated groups on the first moiety molecule at the time the second moiety is mixed in for coupling to take place. In this way, one can avoid the necessity of isolating the activated intermediate of the first moiety. If desired and if the intermediate is stable, however, the reaction product of the uronium salt and first moiety reaction (e.g., the uronium salt activated polysaccharide) can be isolated before the second moiety material (e.g., the protein) is mixed in with it. Also, in accordance with the invention, the first moiety can be activated with the uronium salt reagent, isolated, and stored for later use, as long as it remains stable under the isolation and storage conditions.

The presence of some uronium salt reagent at the time the second moiety is mixed in may not be detrimental because it can promote coupling of the second moiety to the first moiety by continuing to activate the moieties. Actually, the presence of some excess uronium salt reagent when the second moiety is added in this two step protocol may make the overall procedure somewhat of a "blend" of the one and two step procedures.

In general, at least two mechanisms are available for activating a first moiety. In one mechanism, carboxyl groups on the first moiety are activated, and in the other mechanism, hydroxyl groups are activated. The process of the invention can be used with many polysaccharides because they are or can be carboxylated or hydroxylated. Because many polysaccharides naturally contain carboxyl groups as part of their repeat unit, e.g., Neisseria PsC, a separate carboxylation is not always necessary. Typically, some of these carboxyl groups can be modified without destroying the antigenicity of the polysaccharide. These native carboxyls can be used, or carboxylated "arms" can easily be added to the polysaccharide, as described in the examples. In other cases, carboxyl groups can be introduced easily, especially with CDAP. For example, CDAP can be used to derivatize Pneumococcal polysaccharide type 14 ("Pn 14") with 6-aminohexanoic acid. Amine-containing polysaccharides can be carboxylated using glutaric anhydride. Carboxymethyl dextran can be prepared easily from dextran and chloroacetic acid in base, as described by Inman, *Journal of Immunology*, Vol. 114, page 704 (1975) (which article is entirely incorporated herein by reference). Methods for converting various functional groups to carboxyl groups also are well known. Note the discussion in G. T. Hermanson, *Bioconjugate Techniques,* Academic Press, San Diego, Calif., (1996), pg. 187. Thus, many polysaccharides can be carboxylated and activated by the method according to the invention.

As noted above, however, it is not a requirement that the first moiety starting material contain carboxyls. Hydroxyl groups on the first moiety also can be activated with uronium salt reagents. As demonstrated in the examples below, the process of the invention can be used with starting materials that do not contain carboxyls (e.g., Pn 14). Thus, using a first moiety material that contains carboxyls should be viewed as optional.

Different starting materials can be used in the process according to the invention. For example, the first moiety can be a polysaccharide, a high or low molecular weight carbohydrate, or a hydroxylated compound (e.g., a synthetic hydroxylated compound, such as polyvinyl alcohol or polyethylene glycol). Additionally, the first moiety can be a natural or synthetic material that is either soluble or insoluble in water.

Examples of specific polysaccharides for use in the method according to the invention include dextran, carboxylated dextran (such as carboxymethyl dextran), *Neisseria meningiditis* polysaccharide type C, Pneumococcal polysaccharides (such as Pn 14, Pn 6, Pn 19, and Pn 23), and Haemophilus influenza ("PRP") polysaccharide. Examples of suitable high or low molecular weight carbohydrates for use in the invention include sucrose, PRP oligosaccharide, lipopolysaccharide, and lipooligosaccharide. Examples of suitable hydroxylated compounds for use in the invention include polyvinyl alcohol, Ficoll, and polyethylene glycol.

In the reaction process of the invention, the activated first moiety reacts with a second moiety present in the reaction mixture. Suitable examples of materials that can be used as the second moiety include proteins, haptens, peptides, lipoproteins, carbohydrates, organic molecules, spacer molecules, solid phase materials, homobifunctional reagents, or heterobifunctional reagents. This second moiety can be a natural or synthetic material that is either soluble or insoluble in water. The process according to the invention can be used to make conjugates of these first and second moieties, including protein/polysaccharide conjugates, glycosolated protein/protein conjugates and the like. Additionally, an activated first moiety (e.g., an activated polysaccharide) can be coupled to an amino or hydrazide surface in the process of the invention to produce reagents.

Examples of specific suitable proteins for use in this invention include bovine serum albumin, tetanus toxoid, diptheria toxoid, pertussis toxoid, rib protein, intimin, and gD protein. Examples of suitable peptides for use in the invention include LHRH peptide and CFA/I consensus peptide (see F. J. Cassels, et al., *Journal of Industrial Microbiology,* 1996 Annual Meeting for the Society of Industrial Microbiology). Examples of suitable lipoproteins for use in the invention include lipoOspA and lipoD. Examples of suitable haptens include PamCys and monophosphorolipid A. Examples of other carbohydrates for use in the invention include glycosolated proteins and horseradish peroxidase. An example of a suitable organic molecule for use in the invention includes biotin hydrazide. Examples of suitable spacer molecules include hexanediamine and adipic dihydrazide. Examples of suitable solid phase materials for use in the invention include ELISA ("enzyme-linked imnmunosorbent assay") plates, beads, and chromatography media. Examples of suitable heterobifunctional reagents include hydrazido [3 -(2-pyridyl dithio) propionate] and mercaptoethyl amine. An example of a suitable homobifunctional reagent for use in the invention includes cystamine.

Preferred uronium salt reagents for use according to the invention include the members the following group: 2-(1H-Benzotriazole-1-yl)-1,1,3,3-tetramethyluronium hexafluorophosphate ("HBTU"); 2-(1H-Benzotriazole-1-yl)-1,1,3,3-tetramethyluronium tetrafluoroborate ("TBTU"); 2-(5-Norbornene-2,3-dicarboximido)-1,1,3,3-tetramethyluronium tetrafluoroborate ("TNTU"); and O-(N-Succinimidyl)-1,1,3,3-tetramethyluronium tetrafluoroborate ("TSTU"). These uronium salts are available from NovaChem. Additionally, TSTU can be obtained from Aldrich. TSTU and TNTU are particularly preferred uronium salt reagents. Because it is a relatively mild reagent, TSTU is a less harmful crosslinker than carbodiimides. Applicants have observed that TSTU appears to cause much less homopolymerization of proteins than does EDC.

Various vaccines can be made using conjugates produced by the process of the invention. The vaccines include, but are not limited to, the vaccines set forth below:

Diphtheria vaccine
Pertussis (subunit) vaccine
Tetanus vaccine
*H. influenzae,* type b (polyribose phosphate)
*S. pneumoniae,* all serotypes
*E. coli,* endotoxin or J5 antigen (LPS, Lipid A, and Gentabiose)
*E. coli,* O polysaccharides (serotype specific)
Klebsiella, polysaccharides (serotype specific)
*S. aureus,* types 5 and 8 (serotype specific and common protective antigens)
*S. epidermidis,* serotype polysaccharide I, II, and III (and common protective antigens)
*N. meningiditis,* serotype specific or protein antigens
Polio vaccine
Mumps, measles, rubella vaccine
Respiratory Syncytial Virus
Rabies
Hepatitis A, B, C, and others
Human immunodeficiency virus I and II (GP120, GP41, GP160, p24, others)
Herpes simplex types 1 and 2
CMV
EBV
Varicella/Zoster
Malaria
Tuberculosis
*Candida albicans,* other candida
*Pneumocystis carinii*
Mycoplasma
Influenzae virus A and B
Adenovirus
Group A streptococcus
Group B streptococcus, serotypes, Ia, Ib, II, and III
*Pseudomonas aeroginosa* (serotype specific)
Rhinovirus
Parainfluenzae, types 1, 2, and 3
Coronaviruses
Salmonella
Shigella
Rotavirus
Enteroviruses
*Chlamydia trachomatis* and *pneumoniae* (TWAR)
Glycoproteins
Neo-formans cryptococcus As one specific example of the process of the invention, uronium salts can be used to activate lipopolysaccharides or lipooligosaccharides in the manner described in more detail in the examples below. Thereafter, the activated lipopolysaccharide or lipooligosaccharide can be coupled to a protein for use in a vaccine. Antibodies to lipopolysaccharides and lipooligosaccharides can provide protection against sepsis and non-typeable *Haemophilus influenza*. Such conjugates of lipopolysaccharides or lipooligosaccharides with a protein (e.g., tetanus toxoid) fall within this invention.

In the process of the invention, conjugates can be made wherein the weight ratio of the second moiety to the first moiety in the conjugate is greater than 0.05 mg/mg (e.g., 0.05 mg protein/mg polysaccharide). For protein/polysaccharide conjugate vaccines, the weight ratio of protein to polysaccharide can be greater than 0.05, with a range of 0.05 to 7 being preferred, and the range of 0.1 to 2 mg protein per mg of polysaccharide being particularly preferred.

The invention will be described more specifically below in terms of various preferred embodiments and specific examples. These preferred embodiments and specific examples should be construed as being illustrative of the invention, and not as limiting the same. Additionally, certain examples use bovine serum albumin (BSA) as a model protein and/or dextran as a model polysaccharide. Of course, biologically relevant proteins and polysaccharides also can be used in the practice of the invention. Specific examples including biologically relevant proteins and polysaccharides also are included in this application.

Many of the specific examples below include the use of DMAP as a base in the reaction process. Many other bases, however, also can be used. For example, sodium carbonate, sodium hydroxide, triethylamine, or diethylisopropylamine also can be used without departing from the invention.

The following examples also include various abbreviations, standard procedures, and materials that are well known to those skilled in the art. The following information will help one to more readily understand the information included in the following examples. These definitions apply in the following examples, unless there is an indication to the contrary.

Monomeric BSA is used in certain examples because the use of the monomeric protein makes it easier to observe the coupling process as a shift in the molecular weight. The monomeric BSA used in these examples was prepared from Cohn fraction V BSA (from Sigma Chemical Co.) or Intergen low endotoxin BSA (from Intergen Corp.) by brief treatment with 10 mM iodoacetamide in HEPES buffer (described below) at pH 7.3, and then gel filtration on a 2.5×100 cm S100HR column (from Pharmacia) as described in Lees, et al., *Vaccine,* Vol. 14, No. 3, (1996) pp. 190–198 (described above). The dextran was T2000 dextran obtained from Pharmacia. For some experiments, the high molecular weight fraction of the T2000 dextran was used. This material was obtained by passing dextran over a gel filtration column (2.5×100 cm S400 HR), as described above. Tetanus toxoid, the various Pneumococcal polysaccharides, the *Neisseria meningiditis* polysaccharide, and the PRP polysaccharide were obtained from SmithKline Beecham (Rixensart, Belgium). Commercial sources for suitable proteins and polysaccharides for use with the invention include American Tissue Culture Collection of Rockville, Md. and Bema Laboratories of Fla.

"HEPES buffer" (or "HE buffer"), as used in this application, represents a mixture of 0.15 M hydroxyethyl piperazine N'-2-ethane sulfonic acid ("HEPES") and 2 mM ethylenediamine tetraacetate ("EDTA") to provide a solution having a pH of 7.3. "HEPES" refers to HEPES alone, without EDTA (pH=8). "5×HEPES buffer" (or "5×HE buffer") represents a mixture of 0.75 M HEPES and 10 mM EDTA to provide a solution having a pH of 7.3. "2.5× HEPES buffer" represents a mixture of equal volumes of 5×HEPES buffer and saline. "Saline" represents a 0.15 M solution of NaCl in water.

When high performance liquid chromatographs ("HPLC") are conducted, unless indicated to the contrary, a Waters model 626 pump was used with a model 600S controller and a model 486 absorbance detector. Prior to running the HPLC chromatographs, all samples were spin filtered using an ultrafree MC 0.45 μm filter unit. The size exclusion HPLC columns used, unless indicated to the contrary, were Phenomenex Biosep G4000 columns (300× 7.8 mm), equilibrated with 0.1 M potassium phosphate buffer at a pH of 7.3. The run velocity was 1 ml/min. Some runs included the use of a guard column of the same material. Sterile filtering, when performed, was performed on a Millex GV device, unless indicated to the contrary.

The "pH," as used in this application, refers to apparent pH as measured by a Ross electrode (available from Orion Research) or estimated with colorfast pH paper (available from EM Science.)

Furthermore, in this application, unless indicated to the contrary, the presence of amines was determined using a trinitrobenzenesulfonic (TNBS) acid assay, as described by J. Vidal and C. Franci, *J Immunol. Meth.*, Vol. 86, pg. 155 (1986). The presence of hydrazides also was determined using a TNBS assay as described by Qi, et al., *Anal. Chem.*, Vol. 275, pg. 139 (1988). The presence of polysaccharides was determined using the resorcinol/sulfuric acid method of Monsigny, et al., *Anal. Chem.* Vol. 175, pg. 525 (1988), using the relevant polysaccharide standard. The presence of protein was determined using the Coomassie Plus Protein Assay Reagent (available from Pierce Chemical Co., of Rockport, Ill.) (an appropriate protein, such as BSA or tetanus toxoid, was used as the standard). All of these cited documents are entirely incorporated herein by reference.

Finally, where HPLC is used for determining the extent of conjugation (e.g., mg protein/mg polysaccharide), it is calculated from the initial protein/polysaccharide ratio in the starting materials and the percent of the UV absorbance for the conjugated protein peak (based on the total UV absorbance of the protein), as measured by the HPLC.

EXAMPLE 1

In this first example, dextran polysaccharide moieties were coupled to a BSA protein moiety to produce a conjugate. The dextran moieties were both carboxylated and non-carboxylated.

Carboxymethyl dextran ("CM dextran") was prepared at a concentration of 39 mg dextran/mi in saline by the method of Inman, identified above. The non-carboxylated dextran was present at a concentration of 74 mg/ml in saline. The monomeric BSA protein was present at a concentration of 32 mg/ml in 2.5×HEPES buffer having a pH of 7.3. TSTU and DMAP reagents each were present as 0.2 M solutions in DMF.

Sample 1A

For this Sample, 82 μl of the CM dextran material was mixed with 82 μl of water and 86 μl DMF. At time t=0, 10 μl TSTU and 10 μl DMAP were added to the dextran material. At time t=1 minute, an additional 10 μl of TSTU was added, and at time t=2 minutes, an additional 10 μl TSTU was added. During this portion of the procedure, DMAP was added as necessary to maintain the pH of the solution in the range of 8–9. In total, approximately 50 μl of DMAP was added.

At time t=5 minutes, 100 μl of the BSA material was added to the reaction mixture, and the mixture was allowed to react overnight at a temperature of 4° C. to produce the conjugate.

Sample 1B

In Sample 1B, the procedure for Sample 1A was followed, but T2000 dextran was used in place of the CM dextran material.

Sample 1C

For Sample 1C, the procedure for Sample 1A was followed, but 82 μl of saline was substituted for the CM dextran material used in Sample 1A. This Sample was a control sample illustrating the effects of eliminating the polysaccharide material.

The reaction products of Samples 1A through 1C were analyzed by HPLC on a Phenomenex Biosep SEC3000, 7.8×150 cm, equilibrated in 0.1 M $KPO_4$ at a pH of 7.3. It was found that Sample 1A, using CM dextran, produced a BSA/dextran conjugate having about 0.67 mg BSA/mg dextran. Sample 1B, using a non-carboxylated dextran starting material, resulted in a BSA/dextran conjugate having about 0.87 mg BSA/mg dextran. Sample 1C, the control sample which did not include a dextran polysaccharide, showed less than 5% high molecular weight protein. This indicates that only a small amount of dimerization of the protein resulted from the reaction procedure.

FIG. 1 illustrates the HPLC runs for Samples 1A and 1C. As shown in the HPLC for Sample 1A, a very pronounced high molecular weight absorbance peak was found for the conjugate. This high molecular weight peak represents the BSA/TSTU/CM dextran conjugate of Sample 1A. The HPLC run for Control Sample 1C, which included saline substituted for the CM dextran polysaccharide, did not exhibit this high molecular weight peak corresponding to a conjugate.

This Example demonstrates that uronium salts can be used to produce conjugates of proteins with both carboxylated and non-carboxylated polysaccharides. There is minimal homopolymerization of the protein component in this reaction process.

EXAMPLE 2

This Example illustrates that various different polysaccharides can be activated with uronium salt reagents. Furthermore, the polysaccharides in this Example, once activated, were functionalized with either amines or hydrazides. For Samples 2A and 2H, non-carboxylated dextran was used as the polysaccharide. This polysaccharide was activated by the uronium salt reagents and derivatized with both amines (Sample 2A) and hydrazides (Sample 2H). Samples 2B through 2E use clinically relevant Pneumococcal ("Pn") capsular polysaccharides. Samples 2F and 2G demonstrate that uronium salt reagents can be used to activate carboxylated polysaccharides, and Sample 2F further demonstrates that this class of reagents can activate a plant polysaccharide. Sample 2I shows use of the invention with a clinically relevant PRP polysaccharide.

The experimental protocols for performing the activation and derivatization will be described in more detail below. The following reagents were prepared and used in the various experiments described below, unless there is some indication to the contrary: (a) TSTU reagent prepared as a 0.5 M solution in DMF; (b) DMAP reagent prepared as a 0.5 M solution in water; (c) ethylenediamine reagent prepared as a 1 M solution in water; and (d) adipic dihydrazide solution prepared as a 0.5 M solution in water.

Sample 2A

Sample 2A was prepared according to the following protocol. 65 $\mu$l of T2000 dextran, at a concentration of 74 mg/ml, was mixed with 35 $\mu$l of saline and 100 $\mu$l of water. At time t=0, 20 $\mu$l of TSTU (0.5 M in DMF) was added to the solution. At time t=20 seconds, 20 $\mu$l of DMAP (0.5 M in water) was added, and then at t=1 minute and t=1.5 minute, 20 additional $\mu$l of TSTU was added to the reaction mixture. In total, 60 $\mu$l of TSTU was added to the dextran starting material. During the procedure, DMAP was added, as necessary, to maintain the pH of the reaction solution in the range of 8 to 8.5.

At time t2 minutes, 300 $\mu$l of 0.67 M ethylenediamine in water was added. After 1 hour, the reaction mixture was desalted on a P6DG column (from BioRad), equilibrated in saline, and pooled. The resulting material was assayed for amines and dextran, and it was determined that the resulting activated polysaccharide contained 9.4 $NH_2$/100 KDa dextran.

Sample 2B

This Sample describes the activation of a biologically relevant polysaccharide using the uronium salts in the process of the invention.

At time t=0, 20 $\mu$l of TSTU was added to 0.5 ml of a Pn 14 polysaccharide solution, having a concentration of 10 mg Pn 14/ml in water. Immediately thereafter, 20 $\mu$l DMAP was added to the solution. At time t=1 minute, an additional 20 $\mu$l of TSTU was added, and at time t=1.5 minute, an additional 20 $\mu$l TSTU was added. A suitable amount of DMAP was added during this procedure to maintain the reaction solution at a pH of about 8.5. At time t=2 minutes, 200 $\mu$l of the 1 M ethylenediamine solution was added.

After about 1 hour, the reaction mixture was desalted on a P6DG column (available from BioRad), equilibrated with saline. Assays were performed to determine the presence of amines ($NH_2$) and the polysaccharide, and it was determined that this activated polysaccharide contained 7.6 $NH_2$/100 KDa Pn 14.

Sample 2C

In this Sample, the procedure of Sample 2B was followed, except the starting material was 0.5 ml Pn 6 at a concentration of 10 mg/ml in water. After the initial assay, the samples were pooled and concentrated using a Centricon device (available from Amicon). The sample was rerun on the P6DG column and reassayed. It was determined that the resulting activated Pn 6 polysaccharide contained 10.4 $NH_2$/100 KDa Pn 6.

Sample 2D

In this Sample, the procedure of Sample 2B was followed, except the starting material was 0.5 ml Pn 19, having a concentration of 10 mg/ml in saline. It was determined that the resulting activated Pn 19 polysaccharide contained 9.9 $NH_2$/100 KDa Pn 19.

Sample 2E

In this Sample, the procedure of Sample 2C was followed, except the starting material was 0.5 ml Pn 23 having a concentration of 10 mg/ml in saline. It was determined that the resulting activated Pn 23 polysaccharide contained 3.4 $NH_2$/100 KDa Pn23.

Sample 2F

For this Sample, the polysaccharide solution was 0.5 ml pectin (citrus fruit pectin available from Sigma) at a concentration of 10 mg/ml in water, plus 200 $\mu$l sodium carbonate (1M), at a pH of about 9.6. At time t=0, 20 $\mu$l of 0.5 M TSTU (in DMF) was added to this polysaccharide solution. Then, at time t=1 minute, an additional 20 $\mu$l of TSTU was added, and the pH was maintained in the range of 9–9.5 using the 1 M sodium carbonate solution. At time t=3 minutes, 500 $\mu$l of 1M ethylenediamine (in water) was added. This reaction mixture was allowed to stand overnight at room temperature, and then it was desalted on a P6DG column (available from BioRad). It was determined that the resulting activated polysaccharide contained 8.4 $NH_2$/100 KDa Pectin.

Sample 2G

For this Sample, 200 $\mu$l of CM dextran (containing 7.5 carboxyls/100 KDa), at a concentration of 48 mg/ml in saline, was mixed with 200 $\mu$l of water. At time t=0, 20 $\mu$l of TSTU (0.5 M in DMF) was added to the solution. At time t=20 seconds, 20 $\mu$l of DMAP (0.5 M in water) was added, and then at t=1 minute and t=1.5 minute, 20 additional $\mu$l of TSTU was added to the reaction mixture. In total, 60 $\mu$l of TSTU was added to the CM dextran starting material. During the procedure, DMAP was added, as necessary, to maintain the pH of the reaction solution in the range of 8 to 8.5.

At time t=2 minutes, 200 $\mu$l of 0.5 M ethylenediamine (in water) was added. After 1 hour, the reaction mixture was desalted on a P6DG column (from BioRad), equilibrated in saline, pooled, concentrated on a Centricon 30 device (available from Amicon), and desalted again. The resulting material was assayed for amines and dextran, and it was determined that the resulting activated polysaccharide contained 10.6 $NH_2$/100 KDa CM dextran.

Sample 2H

In this Sample, the procedure of Sample 2B was followed, except the starting material was 100 $\mu$l T2000 dextran having a concentration of 55 mg/ml in water. Also, during the reaction procedure, at time t=2 minutes, 200 $\mu$l of the 0.5 M adipic dihydrazide solution was added instead of the 200 $\mu$l of 1 M ethylenediamine solution added in the process of Sample 2B.

It was determined that the resulting activated T2000 dextran polysaccharide contained 8.9 hydrazide ("Hz") per 100 KDa dextran.

Sample 2I

In this Sample, a PRP polysaccharide was activated using a TNTU uronium salt reagent. To do so, 80 µl of 0.3 M TNTU (in NMP) and 48 µl of 0.5 M TEA (in NMP) were mixed into 0.5 ml of PRP (at a concentration of 10 mg/ml) in 2M NaCl. After 2 minutes, 250 µl of 0.5 M hexanediamine in 0.1 M sodium borate (pH=9.3) was added to the above mixture. The reaction proceeded overnight at a temperature of 4° C. The reaction mixture was then desalted on a P6DG column (available from BioRad), equilibrated with saline.

The reaction product was assayed for amines and the polysaccharide, and it was determined that the resulting material had 11.4 $NH_2$ groups/100 kDa PRP.

Conclusion Regarding Example 2

This Example illustrates that uronium salt reagents can be used to derivatize a variety of different polysaccharides and to functionalize the polysaccharides with either amines or hydrazides. Proteins or any other second moieties can be substituted for diamine or dihydrazide and coupled to the activated polysaccharides. Also, this Example shows that clinically relevant polysaccharides can be functionalized by the process of the invention, as well as plant polysaccharides.

EXAMPLE 3

This Example demonstrates the process of the invention wherein the uronium salt reagents are removed before the protein is coupled to the activated polysaccharide.

The polysaccharide starting material was 5 mg of T2000 dextran material, present at a concentration of 74 mg dextran/ml solution (corresponding to about 68 µl of the dextran solution). 68 µl water, 135 µl NMP, 50 µl 0.2 M TSTU (in NMP), and 50 µl 0.2 M DMAP (in NMP) were added to this dextran solution. The pH at the start was about 9.6, and it dropped from this level.

At time t=30 minutes, about 1 ml of water was added. The excess reagents were then removed by ultrafiltration using a Filtron Omega 30 K membrane, 10 ml size, to produce 0.5 ml final volume. An additional 1 ml of water then was added, and the resulting mixture was concentrated to about 400 µl. The polysaccharide was removed from the apparatus, and an additional 100 µl of water was used to rinse the membrane, thereby providing a total volume of about 500 µl.

BSA monomer was added at a ratio of 1.7 mg BSA/mg dextran to this activated polysaccharide solution. The final BSA concentration was about 7.3 mg/ml.

This reaction mixture was allowed to stand overnight at a temperature of about 4° C. An HPLC was conducted (OD 280 nm) to determine the existence of a BSA/dextran conjugate and the amount of BSA material present in the conjugate reaction product. The HPLC was conducted on a Phenomenex SEC3000, 150×7.8 cm, equilibrated with 0.1 M $KPO_4$, pH=7.3, at a run velocity of 1 ml/minute. From HPLC, it was found that 35% of the protein was present in the high molecular weight peak for the conjugate (and 65% was present as free protein). Therefore, the resulting conjugate was found to contain about 0.6 mg BSA/mg dextran.

EXAMPLE 4

For this example, the uronium salt reagent and various other reagents were added to the polysaccharide material at different times. Between additions of the uronium salt reagent, excess reagents were removed by ultrafiltration.

A solution was prepared containing 15 mg dextran, 15 mg BSA monomer, and 3.33 ml saline. At time t=0, 40 µl of 0.3 M TNTU (in NMP) and 12 µl of 1 M TEA (in NMP) were added to the solution. Then, at time t=2 minutes, an additional 6 µl of TEA was added.

At time t=1 hour, the following washing protocol was performed. The mixture was washed by ultrafiltration (on a Filtron Omega 30, 10 ml size). The filtered mixture was diluted to 10 ml with saline and then concentrated to 3 ml. Of this solution, 0.6 ml was removed for analysis.

To the remaining polysaccharide solution, TNTU and TEA were added in the same manner as described above. After 1 hour of reaction time, the wash protocol was again repeated. At this time, 0.6 ml again was removed for analysis.

The TNTU and TEA addition procedure was repeated a third time and again a fourth time, with the washing protocol as described above provided between these procedures. For these third and fourth additions, however, the amount of TNTU and TEA was doubled.

After the fourth addition of TNTU and TEA, after the reaction proceeded for 1.5 hours, the reaction mixture was concentrated to 1.5 ml, and 0.5 ml of this solution was removed for analysis. The remaining material was concentrated to 0.6 ml.

40 µl of TNTU and 10 µl of TEA were added to the remaining 0.6 ml of material. After 1 hour, the mixture was passed over a S400HR gel filtration column. Through analysis of the samples, it was found that after the first addition, the resulting conjugate material contained about 0.043 mg BSA/mg dextran. After the fourth addition, the conjugate contained 0.17 mg BSA/mg dextran.

This Example demonstrates that when the protein and polysaccharide are dilute, there is less coupling then when they are more concentrated. By the repeated addition of reagents, it was possible to significantly increase the amount of coupling. Removal of the used reagent and solvent kept their concentrations low, even when they were added multiple times.

EXAMPLE 5

In this Example, a carbohydrate was coupled to a protein using TSTU to form a conjugate. For this procedure, 20 µl of 0.5 M TSTU (in DMF, corresponding to about 10 µmoles TSTU) and 20 µl of 0.5 M DMAP (in water) were mixed into 200 µl sucrose (corresponding to about 30 µmoles). At time t=1 minute, an additional 20 µl of the TSTU solution and 20 µl of the DMAP solution were added. At time t=1.5 minutes, an additional 20 µl of the TSTU solution and another 20 µl DMAP were added. Then, at time t=2 minutes, 200 µl of 32.2 mg/ml BSA (monomeric) in saline was added to the activated sucrose solution. After about 20 seconds, 20 µl of 1 M sodium carbonate was added, and then another 20 µl of 1 M sodium carbonate was added.

After about 20 minutes, the resulting reaction mixture was desalted on a 1×15 cm P6DG column (available from BioRad), equilibrated with PBS, and the void volumes were pooled. Then, the material was concentrated using a Centricon 30 device (available from Amicon) and again desalted, and finally the void volumes were pooled. The protein content was determined by the BioRad assay, and the carbohydrate content was determined using the resorcinol assay with sucrose as the standard. It was found that the resulting conjugate had 17.5 moles sucrose per mole BSA. This indicated coupling of a low molecular weight carbohydrate to a protein.

EXAMPLE 6

Various uronium salts are used in this example to demonstrate that different salts can be used to activate polysaccharides in the process of the invention. In total, four different uronium salts, namely TSTU, TNTU, HBTU, and TBTU, were tested in this Example.

All of the starting uronium salts were produced in a 0.3 M solution in NMP. DMAP used in this procedure also was present in a 0.3 M solution in NMP. The BSA protein material is monomeric with a concentration of 64.4 mg BSA/ml. This BSA material was mixed 1:1 (by weight) with 5×HEPES buffer (which corresponds to 0.75 M HEPES and 5 mM EDTA to produce a solution having a pH of about 7.3).

To carry out the reaction procedure for this Example, 54 µl of T2000 dextran at a concentration of 74.4 mg/ml (corresponding to 4 mg dextran) was mixed with 28 µl saline, 82 µl water, and 86 µl NMP in each of four different test tubes. Then, at time t=0, 10 µl of one of the uronium salts was added to each test tube so that each test tube contained a different uronium salt. 10 µl of DMAP also was added to each test tube along with the uronium salt. At time t=1 minute, an additional 10 µl of the appropriate uronium salt was added to the corresponding test tube, and again at time t=2 minutes, an additional 10 µl of the appropriate uronium salt was added to the corresponding test tube. During this portion of the reaction procedure, the pH of the solution was maintained in the range of 8–9 with DMAP, and a total of about 50 µl of DMAP was needed in each test tube to maintain the pH in this range.

At the time t=10 minutes, 100 µl of the BSA solution was added to each test tube, which amount corresponds to about 1 mg BSA/mg dextran. The reaction in each test tube was allowed to proceed for about 20 hours, at which time the reaction product was assayed by HPLC on a Phenomenex BioSep G4000 (150×7.8 cm, 50% 0.1 M KPO$_4$, pH=7.3, 50% 0.5 M KCl, 1 ml/minute) monitored at 280 nm. The assay results are tabulated below.

TABLE 1

| Uronium Salt | % HMW BSA |
| --- | --- |
| TSTU | 79% |
| TNTU | 87% |
| HBTU | 36% |
| TBTU | 27% |

These test results confirm that all of the tested uronium salt reagents worked to activate the polysaccharide and supported coupling of the activated polysaccharide to the protein.

EXAMPLE 7

This Example demonstrates that TNTU can be used to activate synthetic polyvinyl alcohol ("PVA"). The PVA was obtained from Aldrich (catalog number 36,062-7). It was 80% hydrolyzed and had an average molecular weight of 9000 to 10,000. The PVA was solubilized in water, with gentle heating, to a concentration of 20 mg/ml. 250 µl of this PVA solution (corresponding to about 5 mg PVA) was mixed with 250 µl hexanediamine to provide a solution having a pH of about 8. At time t=0, 40 µl of 0.3 M TNTU and 24 µl 1 M TEA in NMP were added to the PVA solution. Then, at time t=1 minute, an additional 12 µl of the 1 M TEA solution was added.

The reaction was allowed to proceed overnight. A solid lump formed in the solution, and the mixture was warmed to resolubilize the solid. The resultant solution was then dialyzed exhaustively into saline (volume about 3.5 ml). It was determined that the resulting PVA solution, activated with TNTU, was about 0.113 mM in NH$_2$, which corresponds to more than 6 NH$_2$/100 KDa.

This Example demonstrates that a uronium salt (e.g., TNTU in this example) can activate secondary alcohols. Since PVA is a synthetic polymer (not containing carboxyl groups), this shows that the process of the invention can be used to activate synthetic, non-carboxylated polymers.

EXAMPLE 8

This Example is provided to demonstrate the one step procedure for simultaneously activating and coupling clinically relevant proteins and polysaccharides.

Sample 8A

For this sample, the protein starting material, tetanus toxoid, was present in a saline solution at a concentration of 16.8 mg/ml. The polysaccharide used was a PRP polysaccharide, solubilized at a concentration of 10 mg/ml in 2 M NaCl by rotating for one hour at room temperature. The TNTU activating agent was present in a 0.3 M solution in NMP. The TEA used in this Example was present in a 2 M solution in NMP. Finally, the glycine used was at a 2 M concentration in water, adjusted to pH 8.

For the reaction procedure, 0.5 ml of the PRP solution (corresponding to 5 mg PRP) was combined with 297 µl of the tetanus toxoid solution (corresponding to 5 mg of TT). This mixture was then concentrated to 0.5 ml using a Centricon 50 device (from Amicon).

Thereafter, at time t=0, 50 µl of the TNTU activating agent was added. Approximately 15 seconds later, 20 µl of the TEA was added. After 2 hours, 100 µl of the glycine reagent was added.

The reaction mixture was allowed to stand overnight. Then, the sample was passed over a 1×50 cm S400HR gel filtration column, equilibrated with saline. The high molecular weight fractions were pooled and assayed for tetanus toxoid and PRP. The material was found to have 0.78 mg tetanus toxoid per mg of PRP.

Sample 8B

For this Sample, a tetanus toxoid/Neisseria PsC conjugate was prepared using TNTU as an activating agent to activate the Neisseria PsC. This reaction procedure followed the one-step reaction protocol wherein the protein and polysaccharide are first mixed together, and thereafter, the uronium salt activating reagent is added to this mixture.

First, 238 µl of tetanus toxoid (having a concentration of 16.8 mg/ml) was added to 0.4 ml of Neisseria PsC (having a concentration of 10 mg/ml in saline). This mixture was then concentrated to about 0.3 ml using a Filtron Omega 30 pressure filtration device.

50 µl of 0.3 M TNTU (in NMP) was then added to the concentrated protein/polysaccharide mixture. Thereafter, 50 µl of 1M TEA (in NMP) was added, and shortly thereafter, an additional 25 µl of 1 M TEA was added.

The reaction proceeded overnight at 4° C. The mixture was passed over a S400HR gel filtration column (Pharmacia), 1×50 cm, equilibrated with PBS. The mixture was then sterile filtered on a Millex GV to obtain the high molecular weight fraction.

This reaction product was assayed to determine the tetanus toxoid and Neisseria PsC content. It was found that the resulting conjugate contained 0.32 mg TT/mg Neisseria PsC.

As is evident from the test results, this Example demonstrates the process of the invention wherein the polysaccharide is activated and coupled with the protein in a single process step. Additionally, this Example demonstrates the usefulness of TNTU in producing clinically relevant conjugates with a carboxyl containing polysaccharide.

EXAMPLE 9

This Example describes the use of uronium salt reagents to prepare solid phase reagents. In general, a polysaccharide in liquid media (e.g., aqueous, organic/aqueous mixed, or organic media) is activated with a uronium salt reagent and coupled to an amino-bead, ELISA plate, or other solid phase material. The coupled polysaccharide and solid phase material may be useful, for example, as a diagnostic reagent, such as a solid phase material to absorb specific antibodies for analysis. A more specific example follows.

100 μl of Pn 14 (at 10 μg/ml) in saline is pipetted into the wells of an amino-functionalized ELISA plate (e.g., Nunc "Covalink"). 5 μl of 0.3 M TSTU (in NMP) is pipetted into each well, followed by 5 μl of 0.3 M TEA (in NMP). As controls, saline only, TSTU and TEA only, or Pn 14 only are placed in additional wells. After 1 hour, the wells are washed with saline. The wells are tested for the presence of Pn 14 bound to the ELISA plate using known anti-Pn 14 positive antisera, according to Lees et al., *Vaccine*, 1996, described above.

These ELISA plates then are used for evaluation of anti-Pn 14 antisera.

Other polysaccharides can be coupled to solid phase materials as well. Those skilled in the art will be capable of devising coupling schemes for other solid phase reagents, such as amino or hydrazide microbeads (available from Bangs Laboratories) and amino or hydrazide chromatography media (available from Pharmacia).

EXAMPLE 10

Various Pneumococcal 14 based reagents and conjugates were prepared in this Example. The Pneumococcal based reagent comprises a biotin-Pn14 conjugate, coupled via a spacer (Sample 10A) or directly to the activated polysaccharide (Sample 10B).

Sample 10A

The starting material for this procedure was 0.5 ml Pneumococcal type 14 (available from American Tissue Culture Collection of Rockville, Md.) at a concentration of 10 mg/ml in water. At time t=0, 20 μl of 0.5 M TSTU (in DMF) was added to the polysaccharide, followed immediately by the addition of 20 μl of DMAP (0.5 M in water). At t=1 minute, an additional 20 μl of TSTU was added, and an additional 20 μl TSTU was added at t=1.5 minutes. 200 μl of 1 M ethylenediamine (in water) was added at t=2 minutes. DMAP was added periodically to the reaction solution throughout this procedure, in order to maintain the pH of the solution at about 8.5.

After about an hour, the reaction mixture was desalted on a P6DG column (from BioRad, equilibrated in saline), and the resultant material was assayed for amines and polysaccharides. The material, containing ethylenediamine/TSTU/Pn 14 was determined to contain 7.6 amines/100 kDa Pn 14 at a concentration of 2 mg/ml.

The biotin conjugate was then produced. 300 μl of the ethylenediamine/TSTU/Pn 14 mixture described above (2 mg/ml) was mixed with 50 μl 5×HE. Then, 1.6 mg of sulfo NHS LC biotin (available from BioAffinity Systems) in 60 μl of 50% DMF was added to the mixture. After 1 hour, the reaction mixture was still TNBS positive, so additional solid LC biotin was added. After 2 total hours, the reaction mixture was desalted on a P6DG column (from BioRad), equilibrated with PBS, and the void volumes were pooled.

Sample 10B

This Sample was produced in the same manner as Sample 10A, except at time t=2 minutes, 250 μl of biotincaproic hydrazide (available from Sigma), in 50% DMF was added (the biotin material was poorly soluble). After 1 hour, the undissolved material was removed by centrifuging, and the resulting solution was desalted on a P6DG column (available from BioRad), equilibrated in saline.

To confirm the coupling of the biotin with the Pn 14 in these Samples, an assay for biotin was performed by ELISA, as generally described in E. A. Bayer and M. Wilchek, *Methods of Enzymology*, Vol. 184 (1990), pp. 49–51, which article is entirely incorporated herein by reference. In brief, for this procedure, ELISA immunoassay stripwell plates (available from Nunc Maxisorp) were coated with streptavidin (available from Zymed) at 1 μg/ml in PBS and then incubated in a draft-free environment with the indicated concentrations of biotinylated Pn 14 or control Pn 14. A monoclonal anti-Pn 14 was then used to test for binding of the Pn 14 to the streptavidin coated plates.

The following table illustrates the test results.

TABLE 2

ELISA Absorbance
Assay of Pn 14-Biotin or Pn 14 on Streptavidin-Coated Plates
(10 minute test results)

| Pn 14 (μg/ml) | Sample 10A | Sample 10B | Pn 14 Alone |
| --- | --- | --- | --- |
| 1.0 | 3.311 | 3.252 | 0.094 |
| 0.333 | 3.214 | 2.678 | 0.097 |
| 0.111 | 2.733 | 1.805 | 0.085 |
| 0.037 | 1.980 | 1.051 | 0.087 |
| 0.012 | 0.861 | 0.403 | 0.095 |
| 0.004 | 0.360 | 0.216 | 0.108 |
| 0.001 | 0.166 | 0.142 | 0.092 |
| None | 0.100 | 0.105 | 0.093 |

Primary Antibody: Monoclonal anti-Pn 14 at 1:2000
Secondary Antibody: Rabbit anti-mouse IgG-3-HRP
Substrate: TMB
Blocking: None As is apparent from these assay results, unlabeled control Pn 14 did not bind to the streptavidin coated ELISA plates, as indicated by the background level of the absorbance. The conjugate samples, however, did detachably bind to the plates, even at concentrations as low as 1 ng/ml. This indicates that Samples 10A and 10B contained Pn 14 labeled with biotin.

Sample 10C

For this Sample, a clinically relevant conjugate vaccine was synthesized where a tetanus toxoid protein was coupled to a Pn 14 polysaccharide with a spacer. For this procedure, the NH$_2$/TSTU/Pn14 material produced in Sample 10A was used. The coupling reaction procedure was conducted as follows, which is the same general coupling procedure described in A. Lees, et al., *Vaccine*, Vol. 12, No. 13, (1994), pp. 1160–1166, described above.

For this coupling procedure, 100 μl of 0.75 M HEPES, 10 mM EDTA at a pH of 7.3, and 75 μl 0.1 M N-hydroxysuccinimidyl iodoacetate ("SIA," available from BioAffinity Systems) in DMF were combined with 1.66 mg of the $NH_2$/TSTU/Pn 14 material present in 1.15 ml saline. This reaction produced an iodoacetylated Pn 14 reaction product (Pn 14-SIA).

In a separate procedure, 3 mg of tetanus toxoid, at a concentration of 16.8 mg/mil in saline (corresponding to 180 μl of solution), was mixed with 100 μl of HE and 6 μl of 0.1 M N-succinimidyl S-acetylthioacetate ("SATA," available from BioAffinity Systems) in DMF. This reaction produced a tetanus protein with protected thiols ("TT-SATA").

After three hours, the reaction products above were separately desalted on a 1×15 cm P6DG column (from BioRad), equilibrated in PBS for the tetanus toxoid product and equilibrated in saline for the Pn 14 product. The void volumes of each fraction were concentrated (separately) in a Centricon 30 device (available from Amicon).

At this time, 125 μl of the TT-SATA reaction product was combined with about 300 μl of the Pn 14-SIA reaction product and 50 μl of 5×HE and 0.5 M hydroxylamine. The reaction was allowed to proceed overnight. Then, the reaction was quenched by adding 10 μl of 10 mM mercaptoethanol ("BME") and allowed to stand for one hour. Then, 10 μl of 0.5 M iodoacetamide was added, and this mixture was allowed to stand for 10 minutes. The resulting reaction mixture was passed over an S400HR gel filtration column (available from Pharnacia) (1×50 cm, equilibrated in PBS, 0.25 ml/minute, about 1 ml/tube), and the void volume fraction was obtained. The resulting conjugate was found to have about 1.5 mg tetanus toxoid per mg of Pn 14.

Sample 10D

For this Sample, a tetanus toxoid protein was coupled directly to a Pn 14 polysaccharide using TNTU as an activating agent. Therefore, this Sample demonstrates that a clinically relevant protein/polysaccharide conjugate can be produced using a TNTU activating agent.

First, Pn 14 polysaccharide and tetanus toxoid protein each were mixed into a saline solution, each at a concentration of about 6.3 mg/ml. Then, at time t=0, 24 μl of 0.5 M TNTU in NMP was added to the mixture. 12 μl of 1 M TEA in NMP was then added. At time t=1 minute, an additional 6 μl of 1 M TEA was added to the mixture.

At time t=75 minutes, the reaction was quenched by adding 150 μl of 1 M glycine (pH 8). The mixture was fractionated on an S400HR column (equilibrated in PBS), and the high molecular weight fraction was pooled, sterile filtered, and assayed. It was found that the resulting conjugate material contained 0.44 mg tetanus toxoid per mg of Pn 14.

In addition to demonstrating that a TNTU uronium salt activating agent can be used to produce a clinically relevant conjugate, this Example demonstrates that the activation step and the coupling step can occur in a one step procedure. Notably, in the procedure of this Example, the protein and polysaccharide are mixed together first, and then the activating reagent (TNTU) is added to this mixture. As the polysaccharide is activated by the activating reagent, the protein is immediately available for coupling in a convenient one step procedure.

EXAMPLE 11

In this Example, the immunogenicity of certain conjugates produced using the uronium activating agents was tested.

Sample 11A

To begin the conjugate preparation procedure, 2.5 mg of Pn 14 polysaccharide and 2.5 mg of tetanus toxoid protein were mixed together in a total volume of 350 μl. At time t=0, 24 μl of 0.5 M TNTU (in NMP) was added, and then 12 μl of 1 M TEA (in NMP) was added. At time t=1 minute, an additional 6 μl of 1 M TEA was added.

The reaction was quenched at time t=75 minutes by adding 150 μl of 1 M glycine (pH=8). The reaction mixture was passed over an S400HR gel filtration column, equilibrated in PBS, the high molecular weight fractions were pooled, sterile filtered, and assayed. It was determined that the resulting conjugate had 0.44 mg TT/mg Pn 14.

Sample 11B

For this Sample, the tetanus toxoid-SATA-SIA-$NH_2$/TSTU/Pn 14 conjugate prepared in Example 10C was used. As noted above, this conjugate was found to include 1.5 mg TT/mg Pn 14.

Immunogenicity Data

Sample 11A and Sample 11B were used in a mouse model to test the immunogenicity of the resulting conjugates. Three groups of mice (having four mice per group) were treated with various different immunogens. One group of mice was treated with vaccine conjugate Sample 11A, one group with vaccine conjugate Sample 11B, and one group with Pn 14 alone. On Day 0 each mouse was vaccinated with a priming dosage of the respective immunogen (each immunogen contained 5 μg of Pn 14, either present alone or as part of the conjugate). On Day 14, each mouse received a booster immunization using the same immunogen. The mice were led on Day 28. The sera from the mice of the group were pooled, and an anti-Pn 14 IgG titer as performed giving the following results:

TABLE 3

| Conjugate | Anti-Pn 14 IgG titer |
| --- | --- |
| Sample 11A | 72,900 |
| Sample 11B | 110,284 |
| Pn 14 Only | 326 |

As demonstrated by these test results, the two Samples made according to the invention, using uronium salts, induced excellent immunogenic responses in the mice of the group. As expected, Pn 14 alone induced little immunogenic response.

EXAMPLE 12

For this example, the immunological and bactericidal properties of a conjugate according to the invention were investigated. In this instance, a tetanus toxoid/Neisseria PsC conjugate was prepared using TNTU as an activating agent.

First, 4 mg of tetanus toxoid solution (having a concentration of 19.8 mg/ml) were added to 0.4 ml of Neisseria PsC (having a concentration of 10 mg/ml in saline). The tetanus toxoid material was obtained from Mass Public Health Labs. At time t=0, 50 μl of 0.3 M TNTU (in NMP) was added to the protein and polysaccharide mixture. Thereafter, 25 μl of 2M TEA (in NMP) were added.

The reaction proceeded overnight at 4° C. Then, the mixture was passed over a S400HR gel filtration column (Pharmacia), equilibrated with PBS. The high molecular weight fractions were pooled and then sterile filtered by passing the mixture through a Millex GV device (available from Millipore Corp.). It was determined that the resulting conjugate product contained 0.29 mg TT/mg Neisseria PsC.

This conjugate material was then used in a mouse model to test the immunogenicity of the resulting conjugates. Each of four mice was vaccinated with a priming dosage of the conjugate containing 2.5 μg Neisseria PsC on Day 0. On Day 14, each mouse received a booster immunization of the conjugate in the same amount. The mice were bled on Day 28. The sera from the mice were pooled and assayed by ELISA (0.1 OD end point) for anti-PsC antibodies. Additionally, a bactericidal assay was performed according to the procedure described in K. H. Wong, et al., *Journal of Biological Standards,* Vol. 5 (1977), beginning at page 197 (this article is entirely incorporated herein by reference). The following test results were obtained:

Anti-PsC IgG titer=31,019

Bactericidal titer=1:320.

As is evident from this data, the conjugate according to the invention induced excellent immunogenic responses in the mice of the group. Additionally, an excellent bactericidal effect was induced by the conjugates according to the invention (a bactericidal titer greater than 1:40 is typically considered protective).

OTHER FEATURES OF THE INVENTION

This invention further relates to vaccines, immunogens, and immunological, therapeutic, and diagnostic reagents that can be prepared from the conjugates produced in accordance with the invention. In a vaccine, immunogen, or other immunological, therapeutic, or diagnostic reagent, the conjugates produced according to the invention can be combined with a pharmaceutically acceptable medium or delivery vehicle by conventional techniques known to those skilled in the art. Such vaccines and reagents will contain an effective amount of the conjugate according to the invention, together with a suitable amount of vehicle, so as to provide the form for proper administration to a subject or other intended use. The vaccines may include alum or other adjuvants.

Exemplary pharmaceutically acceptable media or vehicles include, for example, sterile liquids, such as water and oils, including those of petroleum, animal, vegetable, or synthetic origin, such as peanut oil, soybean oil, mineral oil, sesame oil, and the like. Saline is a preferred vehicle when the pharmaceutical composition is administered intravenously. Aqueous dextrose and glycerol solutions also can be employed as liquid vehicles, particularly for injectable solutions. Suitable pharmaceutical vehicles are well known in the art, such as those described in E. W. Martin, Remington's *Pharmaceutical Sciences,* which reference is entirely incorporated herein by reference.

The invention also relates to the method for treating a subject and inducing an immune response by administering an immunostimulatory amount of the vaccine according to the invention. The conjugates according to the invention may be administered to any subject for which the treatment may be beneficial, including mammals, especially humans, horses, cows, pigs, sheep, deer, dogs, and cats, as well as other animals, such as chickens. An "immunostimulatory amount" refers to that amount of vaccine that is able to stimulate the immune response of the subject for prevention, amelioration, diagnosis, or treatment of diseases. The vaccines of the invention may be administered by any suitable route, but they preferably are administered by intravenous, intramuscular, intranasal, or subcutaneous injection.

In addition, the vaccines, immunogens, or immunological reagents in accordance with the invention can be administered for any suitable purpose, such as for therapeutic, prophylactic, or diagnostic purposes.

In describing the invention, applicants have set forth certain theories in an effort to disclose how or why the invention works in the manner in which it works. These theories are set forth for informational purposes only. Applicants are not to be bound by any specific chemical or physical mechanisms or theories of operation.

Additionally, applicants have described several examples and processes for producing conjugates in accordance with the invention. While these procedures may be further optimized (e.g., optimizing the pH conditions during coupling), such optimization of the process and reaction conditions is a matter of routine experimentation.

While the invention has been described in terms of various preferred embodiments and specific examples, those skilled in the art will recognize that various changes and modifications can be made without departing from the spirit and scope of the invention, as defined in the appended claims.

We claim:

1. A method of producing a conjugate vaccine, comprising:

mixing a uronium salt reagent with a soluble first moiety selected from the group of polysaccharides and carbohydrates, wherein the uronium salt reagent has a chemical structure corresponding to formula I:

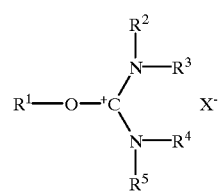

wherein:

$R^1$ is defined as

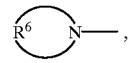

wherein $R^6$ represents the carbon atoms, hydrogen atoms, and optionally one or more heteroatoms, which, together with the nitrogen atom to which they are attached, constitute a 5 to 10 membered heterocyclic ring, which may be substituted or unsubstituted;

wherein $R^2$ and $R^3$ are defined as follows:

$R^2$ represents a hydrogen atom, a substituted or unsubstituted alkyl having 1 to 6 carbon atoms, a substituted or unsubstituted alkenyl having 2 to 6 carbon atoms, or an alkynyl having 2 to 6 carbon atoms;

$R^3$ represents a hydrogen atom, a substituted or unsubstituted alkyl having 1 to 6 carbon atoms, a substituted or unsubstituted alkenyl having 2 to 6 carbon atoms, or an alkynyl having 2 to 6 carbon atoms; or $R^2$ and $R^3$, when taken together, represent the carbon, hydrogen, sulfur, nitrogen, or oxygen atoms necessary to complete a 5 to 7 membered heterocyclic ring with the nitrogen atom to which they are attached, wherein the 5 to 7 membered heterocyclic ring can be substituted or unsubstituted;

wherein $R^4$ and $R^5$ are defined as follows:

$R^4$ represents a hydrogen atom, a substituted or unsubstituted alkyl having 1 to 6 carbon atoms, a substituted or unsubstituted alkenyl having 2 to 6 carbon atoms, or an alkynyl having 2 to 6 carbon atoms;

$R^5$ represents a hydrogen atom, a substituted or unsubstituted alkyl having 1 to 6 carbon atoms, a substituted or unsubstituted alkenyl having 2 to 6 carbon atoms, or an alkynyl having 2 to 6 carbon atoms; or $R^4$ and $R^5$, when taken together, represent the carbon, hydrogen, sulfur, nitrogen, or oxygen atoms necessary to complete a 5 to 7 membered heterocyclic ring with the nitrogen atom to which they are attached, wherein the 5 to 7 membered heterocyclic ring can be substituted or unsubstituted; and $X^-$ represents an acid anion; and mixing a second moiety with the first moiety, wherein the second moiety is selected from the group of proteins, peptides, lipoproteins, haptens, and carbohydrates, whereby the first moiety and the second moiety react to form the conjugate vaccine.

2. A method according to claim 1, wherein the

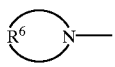

group is a member selected from the group of:

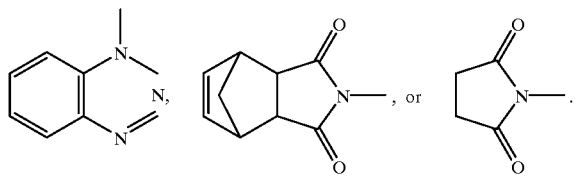

3. A method according to claim 1, wherein the uronium salt reagent is mixed with the first moiety before the second moiety is mixed with the first moiety, wherein a reaction is initiated between the uronium salt reagent and the first moiety.

4. A method according to claim 3, wherein the first moiety is a polysaccharide in solution.

5. A method according to claim 4, further including the step of isolating a product of the reaction between the uronium salt reagent and the polysaccharide before mixing the second moiety with the product.

6. A method according to claim 3, wherein the uronium salt reagent is mixed with the first moiety at least two different times before the second moiety is mixed with the first moiety.

7. A method according to claim 1, wherein the second moiety is mixed with the first moiety before the uronium salt reagent is mixed with the first moiety.

8. A method according to claim 1, wherein the second moiety is mixed with the first moiety at the same time that the uronium salt reagent is mixed with the first moiety.

9. A method according to claim 1, wherein the uronium salt reagent is mixed with the first moiety at least two different times.

10. A method according to claim 1, wherein the acid anion is an anion selected from the group of $Cl^-$, $Br^-$, $F^-$, $I^-$, $PF_6^-$, and $BF_4^-$.

11. A method according to claim 1, wherein the uronium salt reagent is a member selected from the group of 2-(1H-Benzotriazole-1-yl)-1,1,3,3-tetramethyluronium hexafluorophosphate; 2-(1H-Benzotriazole-1-yl)-1,1,3,3-tetramethyluronium tetrafluoroborate; 2-(5-Norbornene-2,3-dicarboximido)-1,1,3,3-tetramethyluronium tetrafluoroborate; and O-(N-Succinimidyl)-1,1,3,3-tetramethyluronium tetrafluoroborate.

12. A method according to claim 1, wherein the first moiety is a polysaccharide in solution.

13. A method according to claim 12, wherein the polysaccharide contains at least one carboxyl group.

14. A method according to claim 1, wherein the first moiety is a polysaccharide selected from the group of Neisseria meningiditis polysaccharide type C, Haemophilus influenza polysaccharide, Pneumococcal polysaccharide, dextran, and carboxylated dextran.

15. A method according to claim 1, wherein the first moiety is a polysaccharide, the method further including the step of carboxylating the polysaccharide before mixing in the uronium salt reagent and before mixing in the second moiety.

16. A method according to claim 15, wherein the polysaccharide is activated by reacting it with a reagent selected from the group of CNBr, 1-cyano-4-dimethylamino pyridinium tetrafluoroborate (CDAP), and a vinylsulfone reagent, and then carboxylated.

17. A method according to claim 12, wherein the second moiety is a protein.

18. A method according to claim 12, wherein the uronium salt reagent is a member selected from the group of 2-(1H-Benzotriazole-1-yl)-1,1,3,3-tetramethyluronium hexafluorophosphate; 2-(1H-Benzotriazole-1-yl)-1,1,3,3-tetramethyluronium tetrafluoroborate; 2-(5-Norbornene-2,3-dicarboximido)-1,1,3,3-tetramethyluronium tetrafluoroborate; and O-(N-Succinimidyl)-1,1,3,3-tetramethyluronium tetrafluoroborate.

19. A method according to claim 1, wherein the first moiety includes at least one carboxyl group.

20. A method according to claim 1, wherein the first moiety includes at least one hydroxyl group.

* * * * *